United States Patent
Soro et al.

(10) Patent No.: US 10,939,820 B2
(45) Date of Patent: *Mar. 9, 2021

(54) WIRELESS PATIENT MONITORING SYSTEM AND METHOD

(71) Applicant: General Electric Company, Schenectady, NY (US)

(72) Inventors: Stanislava Soro, Niskayuna, NY (US); Robert F. Donehoo, Colgate, WI (US); Otto Valtteri Pekander, Helsinki (FI)

(73) Assignee: General Electric Company, Schenectady, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 15/703,633

(22) Filed: Sep. 13, 2017

(65) Prior Publication Data

US 2018/0000345 A1  Jan. 4, 2018

Related U.S. Application Data

(63) Continuation of application No. 15/041,226, filed on Feb. 11, 2016.

(51) Int. Cl.
*A61B 5/00* (2006.01)
*H04Q 9/00* (2006.01)
(Continued)

(52) U.S. Cl.
CPC .......... *A61B 5/0015* (2013.01); *A61B 5/0022* (2013.01); *A61B 5/01* (2013.01);
(Continued)

(58) Field of Classification Search
CPC ...... Y02B 60/50; H04W 52/00; H04W 52/02; H04W 52/0209; H04W 52/0212;
(Continued)

(56) References Cited

U.S. PATENT DOCUMENTS 5,368,026 A  11/1994 Swedlow et al.
5,743,263 A  4/1998 Baker, Jr.
(Continued)

FOREIGN PATENT DOCUMENTS

EP  2470068 A2  7/2012
EP  2432380 A4  3/2013
(Continued)

OTHER PUBLICATIONS

Pending U.S. Appl. No. 14/586,393, filed Dec. 30, 2014, entitled Common Display Unit for a Plurality of Cableless Medical Sensors:, Muuranto et al.

(Continued)

*Primary Examiner* — Benyam Haile
(74) *Attorney, Agent, or Firm* — Andrus Intellectual Property Law, LLP (57) ABSTRACT

A patient monitoring system includes at least two wireless sensing devices, each configured to measure a different physiological parameter from a patient and wirelessly transmit a parameter dataset. The system further includes a receiver that receives each parameter dataset, a processor, and a monitoring regulation module executable on the processor to assign one of the at least two wireless sensing devices as a dominant wireless sensing device and at least one of the remaining wireless sensing devices as a subordinate wireless sensing device. The physiological parameter measured by the dominant wireless sensing device is a key parameter and the parameter dataset transmitted by the dominant wireless sensing device is a key parameter dataset. The key parameter dataset from the dominant wireless sensing device is processed to determine a stability indicator. The subordinate wireless sensing device is then operated based on the stability indicator for the key parameter.

16 Claims, 6 Drawing Sheets

(51) Int. Cl.

| | | |
|---|---|---|
| *H04W 52/02* | (2009.01) | |
| *A61B 5/0408* | (2006.01) | |
| *A61B 5/01* | (2006.01) | |
| *A61B 5/0205* | (2006.01) | |
| *A61B 5/145* | (2006.01) | |
| *A61B 5/02* | (2006.01) | |
| *G16H 40/67* | (2018.01) | |
| *H04W 52/00* | (2009.01) | |

(52) U.S. Cl.
CPC .............. *A61B 5/02* (2013.01); *A61B 5/0205* (2013.01); *A61B 5/0408* (2013.01); *A61B 5/145* (2013.01); *G16H 40/67* (2018.01); *H04Q 9/00* (2013.01); *H04W 52/0225* (2013.01); *H04W 52/0251* (2013.01); *H04W 52/00* (2013.01); *H04W 52/02* (2013.01); *H04W 52/028* (2013.01); *H04W 52/0209* (2013.01); *H04W 52/0212* (2013.01); *H04W 52/0261* (2013.01); *H04W 52/0264* (2013.01); *H04W 52/0274* (2013.01); *Y02D 30/70* (2020.08)

(58) Field of Classification Search
CPC ......... H04W 52/0251; H04W 52/0261; H04W 52/0264; H04W 52/0274; H04W 52/028; H04W 52/0277

See application file for complete search history.

(56) References Cited

U.S. PATENT DOCUMENTS

| | | | |
|---|---|---|---|
| 5,766,228 | A | 6/1998 | Bonnet et al. |
| 5,778,882 | A | 7/1998 | Raymond et al. |
| 5,830,135 | A | 11/1998 | Bosque et al. |
| 6,005,658 | A | 12/1999 | Kaluza et al. |
| 6,163,723 | A * | 12/2000 | Roberts .............. A61N 1/36585 607/18 |
| 6,178,343 | B1 | 1/2001 | Bindszus et al. |
| 6,594,511 | B2 | 7/2003 | Stone et al. |
| 7,803,120 | B2 | 9/2010 | Banet et al. |
| 7,848,810 | B1 | 12/2010 | Nabutovsky et al. |
| 7,993,275 | B2 | 8/2011 | Banet et al. |
| 8,180,440 | B2 | 5/2012 | McCombie et al. |
| 8,200,321 | B2 | 6/2012 | McCombie et al. |
| 8,239,010 | B2 | 8/2012 | Banet et al. |
| 8,321,004 | B2 | 11/2012 | Moon et al. |
| 8,359,080 | B2 | 1/2013 | Diab et al. |
| 8,364,226 | B2 | 1/2013 | Diab et al. |
| 8,364,250 | B2 | 1/2013 | Moon et al. |
| 8,419,649 | B2 | 4/2013 | Banet et al. |
| 8,437,824 | B2 | 5/2013 | Moon et al. |
| 8,442,607 | B2 | 5/2013 | Banet et al. |
| 8,449,469 | B2 | 5/2013 | Banet et al. |
| 8,475,370 | B2 | 7/2013 | McCombie et al. |
| 8,506,480 | B2 | 8/2013 | Banet et al. |
| 8,527,038 | B2 | 9/2013 | Moon et al. |
| 8,545,417 | B2 | 10/2013 | Banet et al. |
| 8,554,297 | B2 | 10/2013 | Moon et al. |
| 8,570,167 | B2 | 10/2013 | Al-Ali |
| 8,571,893 | B2 | 10/2013 | Dashefsky et al. |
| 8,574,161 | B2 | 11/2013 | Banet et al. |
| 8,591,411 | B2 | 11/2013 | Banet et al. |
| 8,594,776 | B2 | 11/2013 | McCombie et al. |
| 8,602,997 | B2 | 12/2013 | Banet et al. |
| 8,622,922 | B2 | 1/2014 | Banet et al. |
| 8,672,854 | B2 | 3/2014 | McCombie et al. |
| 8,721,542 | B2 | 5/2014 | Al-Ali et al. |
| 8,727,977 | B2 | 5/2014 | Banet et al. |
| 8,738,118 | B2 | 5/2014 | Moon et al. |
| 8,740,802 | B2 | 6/2014 | Banet et al. |
| 8,740,807 | B2 | 6/2014 | Banet et al. |
| 8,747,330 | B2 | 6/2014 | Banet et al. |
| 8,808,188 | B2 | 8/2014 | Banet et al. |
| 8,847,740 | B2 | 9/2014 | Kiani et al. |
| 8,852,094 | B2 | 10/2014 | Al-Ali et al. |
| 8,888,700 | B2 | 11/2014 | Banet et al. |
| 8,909,330 | B2 | 12/2014 | McCombie et al. |
| 8,956,293 | B2 | 2/2015 | McCombie et al. |
| 8,956,294 | B2 | 2/2015 | McCombie et al. |
| 8,979,765 | B2 | 3/2015 | Banet et al. |
| 8,989,853 | B2 | 3/2015 | Zong |
| 9,028,407 | B1 | 5/2015 | Bennett-Guerrero |
| 9,055,928 | B2 | 6/2015 | McCombie et al. |
| 9,095,316 | B2 | 8/2015 | Welch et al. |
| 9,149,192 | B2 | 10/2015 | Banet et al. |
| 9,161,700 | B2 | 10/2015 | Banet et al. |
| 9,173,593 | B2 | 11/2015 | Banet et al. |
| 9,173,594 | B2 | 11/2015 | Banet et al. |
| 9,215,986 | B2 | 12/2015 | Banet et al. |
| 2005/0101873 | A1 | 5/2005 | Misczynski et al. |
| 2007/0021680 | A1 | 1/2007 | Mills |
| 2007/0167850 | A1 | 7/2007 | Russell et al. |
| 2008/0300471 | A1 | 12/2008 | Al-Ali et al. |
| 2009/0076343 | A1 | 3/2009 | James et al. |
| 2009/0171167 | A1 | 7/2009 | Baker, Jr. |
| 2009/0275807 | A1 | 11/2009 | Sitzman et al. |
| 2010/0063367 | A1 | 3/2010 | Friedman et al. |
| 2010/0160794 | A1 | 6/2010 | Banet et al. |
| 2010/0160795 | A1 | 6/2010 | Banet et al. |
| 2010/0160796 | A1 | 6/2010 | Banet et al. |
| 2010/0160797 | A1 | 6/2010 | Banet et al. |
| 2010/0160798 | A1 | 6/2010 | Banet et al. |
| 2010/0168589 | A1 | 7/2010 | Banet et al. |
| 2011/0080294 | A1 | 4/2011 | Tanishima et al. |
| 2011/0224498 | A1 | 9/2011 | Banet et al. |
| 2011/0224499 | A1 | 9/2011 | Banet et al. |
| 2011/0224500 | A1 | 9/2011 | Banet et al. |
| 2011/0224506 | A1 | 9/2011 | Moon et al. |
| 2011/0224507 | A1 | 9/2011 | Banet et al. |
| 2011/0224508 | A1 | 9/2011 | Moon |
| 2011/0224556 | A1 | 9/2011 | Moon et al. |
| 2011/0224557 | A1 | 9/2011 | Banet et al. |
| 2011/0224564 | A1 | 9/2011 | Moon et al. |
| 2011/0257489 | A1 | 10/2011 | Banet et al. |
| 2011/0257551 | A1 | 10/2011 | Banet et al. |
| 2011/0257552 | A1 | 10/2011 | Banet et al. |
| 2011/0257553 | A1 | 10/2011 | Banet et al. |
| 2011/0257554 | A1 | 10/2011 | Banet et al. |
| 2011/0257555 | A1 | 10/2011 | Banet et al. |
| 2011/0288421 | A1 | 11/2011 | Banet et al. |
| 2012/0029300 | A1 | 2/2012 | Paquet |
| 2012/0108983 | A1 | 5/2012 | Banet et al. |
| 2012/0190949 | A1 | 7/2012 | McCombie et al. |
| 2012/0203491 | A1 | 8/2012 | Sun et al. |
| 2013/0109937 | A1 | 5/2013 | Banet et al. |
| 2013/0116515 | A1 | 5/2013 | Banet et al. |
| 2014/0025010 | A1 | 1/2014 | Stroup et al. |
| 2014/0031787 | A1 * | 1/2014 | Burnes .............. A61M 5/14276 604/505 |
| 2014/0081099 | A1 | 3/2014 | Banet et al. |
| 2014/0088385 | A1 | 3/2014 | Moon et al. |
| 2014/0142445 | A1 | 5/2014 | Banet et al. |
| 2014/0163393 | A1 | 6/2014 | McCombie et al. |
| 2014/0200415 | A1 | 7/2014 | McCombie et al. |
| 2014/0235964 | A1 | 8/2014 | Banet et al. |
| 2014/0257056 | A1 | 9/2014 | Moon et al. |
| 2014/0275818 | A1 | 9/2014 | Kassem et al. |
| 2014/0276145 | A1 | 9/2014 | Banet et al. |
| 2014/0276175 | A1 | 9/2014 | Banet et al. |
| 2014/0301893 | A1 | 10/2014 | Stroup et al. |
| 2015/0042466 | A1 | 2/2015 | Kiani et al. |
| 2015/0164437 | A1 | 6/2015 | McCombie et al. |
| 2015/0196257 | A1 | 7/2015 | Yousefi et al. |
| 2015/0208966 | A1 | 7/2015 | Al-Ali |
| 2015/0282717 | A1 | 10/2015 | McCombie et al. |
| 2016/0262641 | A1 | 9/2016 | Kurzenberger |

FOREIGN PATENT DOCUMENTS

| | | | |
|---|---|---|---|
| EP | 2162059 | A4 | 10/2013 |
| EP | 2470067 | A4 | 10/2013 |
| EP | 2560550 | A4 | 12/2013 |

(56) References Cited

FOREIGN PATENT DOCUMENTS

| | | | |
|---|---|---|---|
| EP | 2675346 A1 | 12/2013 |
| EP | 2675348 A1 | 12/2013 |
| EP | 2775917 A2 | 9/2014 |
| EP | 2432378 A4 | 12/2014 |
| EP | 24442709 A4 | 12/2014 |
| EP | 2519144 A4 | 3/2015 |
| EP | 2658440 A4 | 4/2015 |
| EP | 2544584 A4 | 7/2015 |
| EP | 2910182 A2 | 8/2015 |
| WO | 2010135516 A2 | 11/2010 |
| WO | 2010148205 A1 | 12/2010 |
| WO | 2011032132 A2 | 3/2011 |
| WO | 2011032132 A3 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |
| WO | 2010135518 A1 | 11/2011 |
| WO | 2012077113 A2 | 6/2012 |
| WO | 2012092303 A1 | 7/2012 |
| WO | 2012112885 A1 | 8/2012 |
| WO | 2012112891 A1 | 8/2012 |
| WO | 2013071014 A2 | 5/2013 |
| WO | 2013071014 A3 | 5/2013 |
| WO | 2014015254 A1 | 1/2014 |
| WO | 2014165620 A1 | 10/2014 |
| WO | 2015120330 A1 | 8/2015 |
| WO | 2015173539 A1 | 11/2015 |

OTHER PUBLICATIONS

International Search Report and Written Opinion for PCT/US20171016530, dated May 19, 2017, 12 pages.
Extended European Search Report dated Jun. 28, 2019 for Application No. 17750600.3.

* cited by examiner

WIRELESS PATIENT MONITORING SYSTEM AND METHOD

CROSS REFERENCE TO RELATED APPLICATION

This application is a continuation of U.S. patent application Ser. No. 15/041,226, filed Feb. 11, 2016, which is incorporated herein by reference in entirety.

BACKGROUND

The present disclosure relates generally to medical devices and, more specifically, to medical monitoring devices for monitoring a patient's physiology and health status.

In the field of medicine, physicians often desire to monitor multiple physiological characteristics of their patients. Oftentimes, patient monitoring involves the use of several separate monitoring devices simultaneously, such as a pulse oximeter, a blood pressure monitor, a heart monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to a single monitor, resulting in multiple wires running across the patient's body. Thus, currently available patient monitoring devices often inhibit patient movement, requiring a patient to stay in one location or to transport a large monitor with them when they move from one place to another.

Further, currently available monitoring devices are often power intensive and either require being plugged in to a wall outlet or require large battery units that have to be replaced and recharged every few hours. Thus, monitoring multiple patient parameters is power intensive and battery replacement is costly in labor and parts. Thus, frequent monitoring is often avoided in order to limit cost and patient discomfort, and instead patient parameters are infrequently spot checked, such as by periodic nurse visits one or a few times a day. While there are some patients that require continuous, real-time monitoring, such as those patients experiencing a critical health condition, the vast majority of patients need only periodic monitoring to check that their condition has not changed. However, patients that are not being regularly monitored may encounter risky health situations that go undetected for a period of time, such as where rapid changes occur in physiological parameters that are not checked by a clinician until hours later or until a critical situation occurs.

SUMMARY

The present disclosure generally relates to a patient monitoring system and method.

A patient monitoring system includes at least two wireless sensing devices, each wireless sensing device configured to measure a different physiological parameter from a patient and wirelessly transmit a parameter dataset. The system further includes a receiver that receives each parameter dataset from each of the at least two wireless sensing devices, a processor, and a monitoring regulation module executable on the processor. The monitoring regulation module is executable to assign one of the at least two wireless sensing devices as a dominant wireless sensing device and at least one of the remaining wireless sensing devices as a subordinate wireless sensing device. The physiological parameter measured by the dominant wireless sensing device is a key parameter and the parameter dataset transmitted by the dominant wireless sensing device is a key parameter dataset. The key parameter dataset from the dominant wireless sensing device is processed to determine a stability indicator for the key parameter. The subordinate wireless sensing device is then operated based on the stability indicator for the key parameter.

One embodiment of a method of monitoring a patient includes providing two or more wireless sensing devices, each wireless sensing device configured to measure a different physiological parameter from a patient. Each wireless sensing device is communicatively connected to a computing system having a processor. The method further includes assigning at the processor one of the at least two wireless sensing devices as a dominant wireless sensing device, and assigning at least one of the remaining wireless sensing devices as a subordinate wireless sensing device. The dominant wireless sensing device is then operated to measure a key parameter from the patient and wirelessly transmit a key parameter dataset. The method further includes processing the key parameter dataset to determine a stability indicator for the key parameter, and selectively operating the subordinate wireless sensing device based on the stability indicator for the key parameter.

Various other features, objects and advantages of the invention will be made apparent from the following description taken together with the drawings.

BRIEF DESCRIPTION OF THE DRAWINGS

The drawings illustrate the best mode presently contemplated of carrying out the disclosure. In the drawings.

DETAILED DESCRIPTION

The present inventors have recognized that wireless monitoring systems are desirable for patient comfort, for example to provide more comfort and mobility to the patient being monitored. The patient's movement is not inhibited by wires between sensor devices and/or computing devices that collect and process the physiological data from the patient. Thus, small sensing devices and sensors that can be easily attached to the patient's body are desirable, such as sensing devices that are wearable portable computing devices. In order to do so, the size of the wireless sensing devices must be small. The present inventors have recognized that an important aspect of decreasing the size and weight of wireless sensing devices is decreasing battery size, and that a weakness in the development of wireless sensing devices has been power consumption and requirement for long battery times.

In view of their recognition of problems and challenges in the development of wireless sensing devices, the present inventors developed the disclosed system and method to minimize power consumption of the wireless sensing devices. As provided herein, battery demand for each wireless sensing device, and thus power requirements for the system as a whole, are decreased by selectively and intelligently operating one or more of the wireless sensing devices on an infrequent basis when the patient's condition is stable and continuous patient monitoring is unnecessary. In the patient monitoring method and system disclosed herein, a dominant wireless sensing device is assigned, such as based on the patient's condition and/or medical or treatment history, and other wireless sensing devices in the system are controlled based on the condition of the patient as determined by the data gathered from the dominant wireless sensing device. Accordingly, the wireless sensing devices are intelligently controlled to enable maximum continuous patient monitoring capabilities when necessary, but can be operated in a reduced monitoring mode when the patient seems stable in order to reduce the power requirements of the wireless sensing devices and increase the battery life of those devices. This will decrease the cost associated with the wireless monitoring system as a whole, including reducing the demand on clinicians to change and charge batteries for the subordinate devices, decreasing the wear on the subordinate devices, while providing sufficient patient monitoring such that deterioration of the patient condition will be timely detected.

Another benefit of the system and method disclosed herein is that the system automatically determines when the patient condition has deteriorated based on the data gathered from the dominant wireless sensing device and automatically initiates increased or continuous monitoring by all wireless sensing devices. Thus, when a clinician responds to an alarm condition, recent monitoring data is already available and is being updated for all relevant physiological parameters monitored by the system. This is an improvement over prior art systems, where clinicians responding to an alarm condition are required to initiate monitoring by various monitoring or sensing devices and wait for those devices to produce measurements in order to fully assess the patient's condition.

In various embodiments, wireless sensing devices measuring different physiological parameters may be networked to a central hub or primary sensing device that controls the wireless sensing devices in the network. The hub may communicate with a central, host network, such as of the medical facility. In another embodiment, the wireless sensing devices may communicate with the host network that calculates the patient stability index and assigns the measurement intervals. There, the wireless sensing devices may communicate with the host network directly, or indirectly through the hub. For example the hub may serve as an amplifier and/or router for communication between the wireless sensing devices and the host network.

Figure 1:
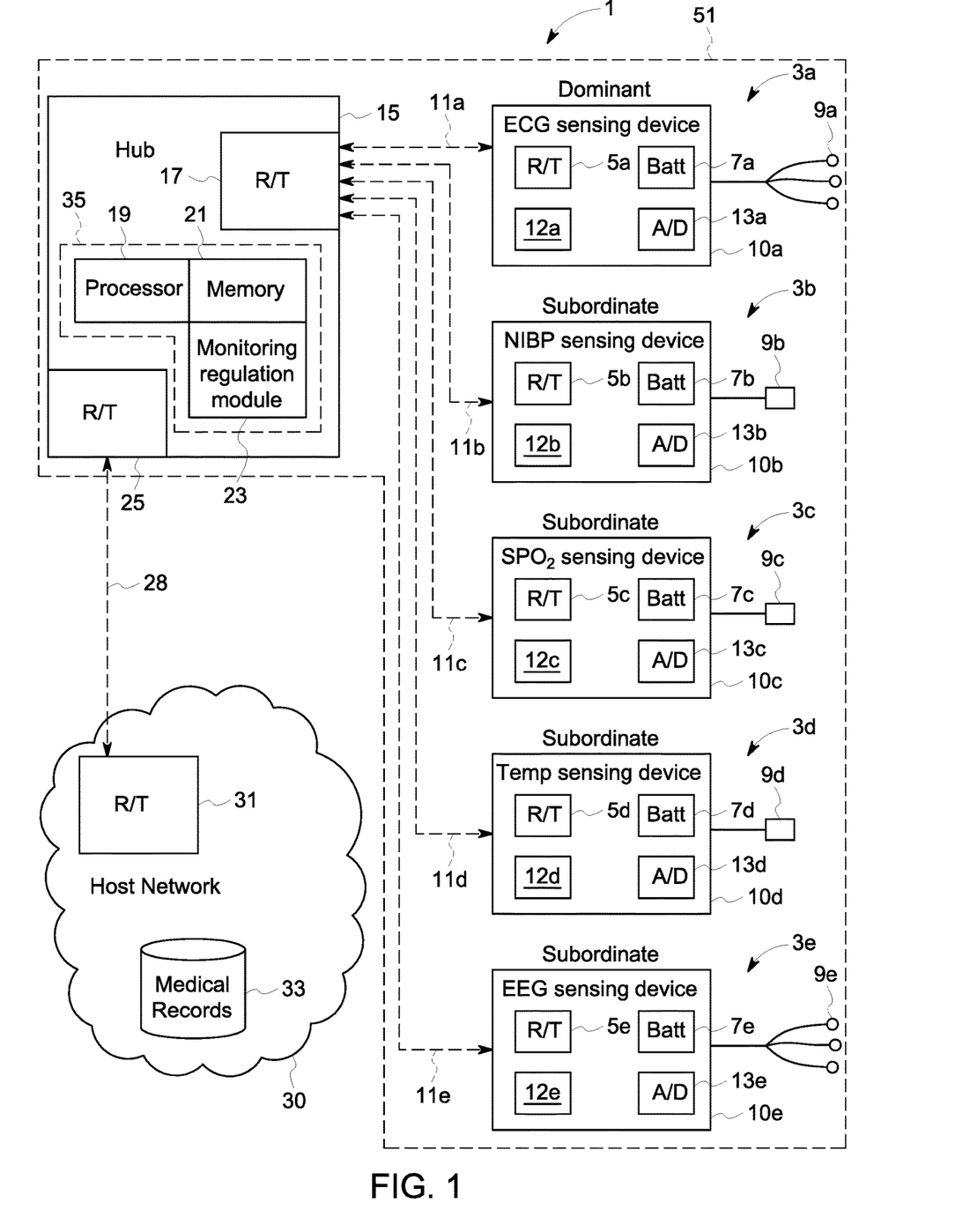
FIG. 1 provides a schematic diagram of one embodiment of a wireless patient monitoring system.

FIG. 1 depicts one embodiment of a patient monitoring system 1 containing five wireless sensing devices 3a-3e in wireless communication with a hub device 15 to form monitoring network 51. For example, the hub device 15 may be attached to the patient's body, placed on or near the patient's bed, or positioned within range of the patient, such as in the same room as the patient. The hub device 15 may be a separate, stand alone device, or it may be incorporated and/or housed with another device within the system 1, such as housed with one of the wireless sensing devices 3a-3e. The hub device 15 is also in wireless communication with a host network 30 that contains medical records database 33.

Each wireless sensing device 3a-3e contains one or more sensors 9a-9e for measuring a physiological parameter from a patient, and also includes a base unit 10a-10e that receives the physiological parameter measurements from the sensors 9a-9e and transmits a parameter dataset based on those measurements to the hub device 15 via communication link 11a-11e. The sensors 9a-9e may be connected to the respective base unit 10a-10e by wired or wireless means. The sensors 9a-9e may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, or the like.

The depicted embodiments include five wireless sensing devices 3a-3e in the monitoring network 51. A first wireless sensing device 3a is an ECG sensing device having sensors 9a that are ECG electrodes. A second wireless sensing device 3b is a non-invasive blood pressure (NIBP) sensing device with a sensor 9b that is a blood pressure cuff including pressure sensors. A third wireless sensing device 3c is a peripheral oxygen saturation (SpO2) monitor having sensor 9c that is a pulse oximetry sensor, such as a standard pulse oximetry sensor configured for placement on a patient's fingertip. A fourth wireless sensing device 3d is a temperature monitor having sensor 9d that is a temperature sensor. The depicted embodiment of the system 1 further includes a fifth wireless sensing device 3e that is an EEG monitor having sensors 9e that are EEG electrodes. It should be understood that the patient monitoring system 1 of the present disclosure is not limited to the examples of sensor devices provided, but may be configured and employed to sense and monitor any clinical parameter. The examples provided herein are for the purposes of demonstrating the invention and should not be considered limiting.

The base units 10a-10e of each of the exemplary wireless sensing devices 3a-3e may include analog-to-digital (A/D) converters 13a-13e, which may be any devices or logic sets capable of digitizing analog physiological signals recorded by the associated sensors 9a-9e. For example, the A/D converters 13a-13e may be Analog Front End (AFE) devices. The base units 10a-10e may further include processors 12a-12e that receive the digital physiological data from the A/D converters 13a-13e and create a parameter dataset for transmission to the hub device 15 and for the host network 30. Each base unit 10a-10e may be configured differently depending on the type of wireless sensing device, and may be configured to perform various signal processing functions and or sensor control functions. To provide just a few examples, the processor 12a in the ECG sensing device 3a may be configured to filter the digital signal from the ECG sensors 9a to remove artifact and/or to perform various calculations and determinations based on the recorded cardiac data, such as heart rate, QRS interval, ST-T interval, or the like. The processor 12b in the NIBP sensing device 3b may be configured, for example, to process the physiological data recorded by the sensors 9b in a blood pressure cuff to calculate systolic, diastolic, and mean blood pressure values for the patient. The processor 12c of the SpO2 sensing device 3c may be configured to determine a blood oxygenation value for the patient based on the digitized signal received from the pulse oximetry sensor 9c. The processor 12d of the temperature sensing device 3d may be configured to, for example, determine a temperature for the patient, such as a mean temperature based on the digitized temperature data received from the thermal sensor 9d. And the process or 12e of the EEG sensing device 3e may be configured, for example, to determine a depth of anesthesia measurement value, such as an entropy value or a sedation responsiveness index value.

Accordingly, the processor 12a-12e may develop a datasets that, in addition to the recorded physiological data, also include values measured and/or calculated from the recorded physiological data. The respective processors 12a-12e may then control a receiver/transmitter 5a-5e in the relevant wireless sensing device 3a-3e to transmit parameter datasets to the hub device 15 via communication link 11a-11e. The parameter dataset transmitted from the respective wireless sensing devices 3a-3e may include the raw digitized physiological data, filtered digitized physiological data, and/or processed data indicating information about the respective physiological parameter measured from the patient.

In other embodiments, the processors 12a-12e may not perform any signal processing tasks and may simply be configured to perform necessary control functions for the respective wireless sensing device 3a-3e. In such an embodiment, the parameter data set transmitted by the respective processor 12a-12e may simply be the digitized raw data or digitized filter data from the various sensor devices 9a-9e.

Each wireless sensing device 3a-3e includes a battery 7a-7e that stores energy and powers the various aspects of the wireless monitor. Each processor 12a-12e may further include power management capabilities, especially where the respective wireless sensing device 3a-3e contains more demanding electromechanical aspects. Each processor 12a-12e may monitor a battery status 43a-43e (FIG. 3), such as a charge level of the relevant battery 7a-7e. The processor 12a-12e may communicate the battery status to the hub device 15 by the communication link 11a-11e. Alternatively or additionally, the processor 12a-12e may control a local display on the wireless sensing device 3a-3e to display the battery status 43a-43e, and/or may control the emission of an audio and/or visual alert regarding the battery status 43a-43e.

The receiver/transmitter 5a-5e of each wireless sensing device 3a-3e in the monitoring network 51 communicates via the respective communication link 11a-11e with the receiver/transmitter 17 of the hub device 15, which may include separate receiving and transmitting devices or may include an integrated device providing both functions, such as a transceiver. The receiver/transmitters 5a-5e of the wireless sensing devices 3a-3e and the receiver/transmitter 17 of the hub device 15 may be any radio frequency devices known in the art for wirelessly transmitting data between two points. In one embodiment, the receiver/transmitters 5a-5e and 17 in the monitoring network 51 may be body area network (BAN) devices, such as medical body area network (MBAN) devices. For example, the wireless sensing devices 3a-3e may be wearable or portable computing devices in communication with a hub device 15 positioned in proximity of the patient. Other examples of radio protocols that could be used for the monitoring network 51 include, but are not limited to, Bluetooth, Bluetooth Low Energy (BLE), ANT, and ZigBee.

The hub device 15 may further include computing system 35 having processor 19 and memory 21. The hub device 15 may serve to control the wireless sensing devices 3a-3e, and thus may transmit operation commands 45a-45e (FIG. 3) to the respective wireless sensing devices 3a-3e via the communication link 11a-11e to control their monitoring operations. The hub device 15 may contain a monitoring regulation module 23 that is a set of software instructions stored in memory and executable on the processor to assess the physiological data collected by the wireless sensing devices 3a-3e and determine a patient condition therefrom, and to control the respective wireless sensing devices 3a-3e according to the patient condition.

For example, the monitoring regulation module 23 may be configured to assign one or the wireless sensing devices 3a-3e as a dominant wireless sensing device that will be used to gauge the patient's condition and to control the frequency of operation of one or more of the other wireless sensing devices in the monitoring network 51, which becomes the subordinate wireless sensing devices. The physiological parameter measured by the dominant wireless sensing device is a key parameter that is used to assess the stability of the patient's condition based on the data measured from the dominant wireless sensing device, the key parameter dataset. The key parameter and the dominant wireless sensing device may be selected based on a diagnosis or a treatment history for the patient. For example, a patient being treated for a particular condition may be assigned a key parameter that is most relevant to monitoring the patient's condition, such as the physiological parameter most associated with or most impacted by the patient's condition or diagnosis. Likewise, if the patient is undergoing or recovering from a particular treatment or procedure, then the key parameter may be the physiological parameter that is most likely to be impacted or to signal complications associated with recovery from the procedure. For instance, electrical activity of the heart is likely to be a key parameter for a patient that is diagnosed with and/or being treated for a heart condition or has recently undergone a cardiac procedure. In that instance, the wireless ECG sensing device 3a may be assigned as the dominant wireless sensing device, and one or more of the remaining wireless sensing devices may be subordinate wireless sensing devices controlled based on the key parameter dataset measured by the ECG sensing device 3a, which is the dominant wireless sensing device.

The monitoring regulation module 23 may process the key parameter dataset 41a (see FIG. 3) from the dominant wireless sensing device to determine a stability indicator for the key parameter, and the subordinate wireless sensing devices may be selectively operated based on that stability indicator. For example, if the stability indicator for the key parameter is within a range that can be considered "stable", then the patient condition is assumed to be stable and the subordinate wireless monitoring devices may be operated in a way to conserve their power consumption.

As illustrated in the embodiment shown in FIG. 1, the ECG sensing device 3a is assigned as the dominant wireless sensing device, and the remaining wireless sensing device 3b-3e in the monitoring network 51 are assigned as the subordinate wireless sensing devices. In other embodiments, some subset of the remaining wireless sensing devices 3b-3e may be assigned as subordinate wireless sensing devices and controlled based on the dominant wireless sensing device 3a. In that embodiment, those wireless sensing devices not assigned as subordinates could be independently controlled. In the depicted embodiment, the dominant ECG sensing device 3a may be operated to continuously monitor the electrical output of the heart as the key parameter for assessing the patient's condition. The output of the dominant ECG sensing device, key parameter dataset 41a, may then be continually processed to determine a stability indicator for the ECG. The remaining wireless sensing devices 3b-3e may then be selectively operated based on the stability indicator. For example, as explained in more detail herein, one or more of the subordinate sensing devices may be turned off and only activated if the key ECG parameter dataset is determined to be unstable. Alternatively or additionally, one or more of the subordinate wireless sensing devices may be operated at a minimum measurement interval, which may be a minimum interval set for each wireless sensing device individually.

For example, a minimum measurement interval may be stored for each subordinate wireless sensing device 3b-3e and the monitoring regulation module 23 may instruct operation of each subordinate wireless sensing device 3b-3e at its minimum measurement interval if the stability index indicates that the key parameter dataset 41a is stable. If the stability index indicates that the key parameter is unstable, the monitoring regulation module 23 may instruct one or more of the subordinate wireless sensing devices 3b-3e to increase the monitoring frequency above the minimum measurement interval as appropriate based on the degree of instability indicated by the patient condition index. For example, the monitoring regulation module 23 may increase the measurement interval proportionally to the level of the stability index, and may instruct any level of monitoring between the minimum measurement interval for each subordinate wireless sensing device and continuous monitoring for each subordinate sensing device depending on the stability index. The minimum measurement interval may be different for each wireless sensing device 3a-3e, and may account for the patient's diagnosis, medical history, procedure history, previous monitoring data, etc. For example, the minimum measurement interval may be set to zero for a wireless sensing device measuring a parameter that is unimportant to the general monitoring of a patient, but might provide important information if the patient's condition begins to deteriorate. In that instance, that subordinate wireless monitoring device may be turned off completely or operated in a low power mode unless the stability indicator for the key parameter is outside of the stable range.

In another embodiment, the dominant wireless sensing device may not be operated continuously, but may be operated at a measurement interval. For example, this may be appropriate where the key parameter is one that takes a period of time to monitor or determine, such as NIBP. In that case, the dominant wireless sensing device may be operated at a frequent and regular interval. Thus, a minimum measurement interval may also be set for the dominant wireless monitor that may be utilized when the stability index is in the stable range. The monitoring regulation module 23 may then increase the measurement frequency proportional to the stability index as the stability index veers out of the normal range, such as increasing the measurement interval to continuous monitoring operation or the most frequent monitoring interval possible given the operating constraints of the relevant wireless monitoring device. The minimum measurement interval may be set relatively high to account for the fact that the relevant wireless sensing device is the dominant device.

The stability index is an indictor of the stability of the key parameter measured by the dominant wireless sensing device. For example, the stability index may be any value that indicates whether the key parameter is in a normal range for the patient and remains unchanged for a period of time. The stability index may be determined based on whether the key parameter dataset contains values within a predetermined range, which could be a patient-specific normal range developed based on relevant physiological data previously recorded from the patient, or could be a population-normal range for the demographic relevant to the patient. To provide just one exemplary embodiment, the stability index may be a value on a linear scale between stable and critical, such as on a scale between 1 and 10, where 1 represents that the values in the key parameter dataset are squarely within a stringent threshold range representing normal for the patient and has been in that range for at least a predetermined amount of time, and 10 represents a critically unstable, life threatening emergency that requires immediate intervention by a clinician. In other embodiments, the stability index may be any series of values capable of being used by the software algorithm of the monitoring regulation module 23 to represent the stability of the key parameter dataset 41a being measured by the dominant wireless sensing device.

For example, people with chronic heart problems oftentimes experience irregular respiration, and thus for such patients it may be appropriate to set respiration as the key parameter. In such an embodiment, the stability index may be calculated as the standard deviation of the respiratory frequency distribution. The value of the respiratory stability index can be classified as within normal range or out of normal range.

In certain embodiments, the monitoring regulation module 23 may be configured such that the key parameter and dominant wireless sensing device are rotated amongst at least two of the wireless sensing devices in the monitoring network 51. For example, two or more of the wireless sensing devices 3a-3e may be designated based on the patient's condition, diagnosis, treatment history, etc., and the dominant designation may be rotated amongst those sensors. For example, a monitoring system 1 for a patient with a diagnosed cardiac issue may have the wireless ECG sensing device 3a and the wireless SpO2 sensing device 3c assigned as the possible dominant wireless sensing devices, and the assignment of the dominant position may be traded between those two wireless sensing devices. Alternatively or additionally, the assignment of the dominant wireless sensing device may be rotated between wireless sensing devices on a periodic basis. The change to a new dominant wireless sensing device may be made based on any number of factors. For example, a new dominant wireless sensing device may be assigned between the possible dominant devices if the current dominant wireless sensing device is indicating low battery power or is malfunctioning. Alternatively or additionally, a new dominant wireless sensing device may be selected and assigned based on the parameter datasets collected by the subordinate wireless sensing devices, such as if a periodic check by one of the subordinate wireless sensing devices indicate a change in the relevant monitored parameter. In that instance, the parameter dataset indicating the change may be assigned as the new key parameter dataset, either for a period of time or indefinitely, and the associated wireless sensing device may be assigned as the new dominant wireless sensing device.

The hub device 15 may communicate with a host network 30 via a wireless communication link 28, such as to transmit the parameter datasets for the respective wireless sensing devices 3a-3e for storage in the patient's medical record. The hub 15 has receiver/transmitter 25 that communicates with a receiver/transmitter 31 associated with the host network 30 on communication link 28, which may operate according to a network protocol appropriate for longer-range wireless transmissions, such as on the wireless medical telemetry service (WMTS) spectrum or on a Wi-Fi-compliant wireless local area network (LAN). The host network 30 may be, for example, a local computer network having servers housed within a medical facility treating the patient, or it may be a cloud-based system hosted by a cloud computing provider. The host network 30 may include a medical records database 33 housing the medical records for the patient, which may be updated to store the parameter datasets recorded and transmitted by the various wireless sensing devices 3a-3e. The host network 30 may further include other patient care databases, such as for monitoring, assessing, and storing particular patient monitoring data. For example, the host network may include an ECG database, such as the MUSE ECG management system produced by General Electric Company of Schenectady, N.Y.

In various embodiments, the hub device 15 may contain software for processing the physiological signals recorded by the various wireless sensing devices 3a-3e. For example, in one embodiment the individual wireless sensing device 3a-3e may perform minimal or no signal processing on the physiological data measured from the patient, and may simply transmit the digitized physiological data recorded from the respective sensors 9a-9e. Software stored in the hub device 15 may then be executed on the processor 19 to calculate various useful parameters from the physiological data, as is explained above with respect to the exemplary wireless sensing devices 3a-3d depicted in FIG. 1. In still other embodiments, minimal or no signal processing may be performed in the hub device 15, and the hub device 15 may simply serve to relay the parameter datasets from the wireless sensing devices 3a-3e to the host network 30. In such an embodiment, the computing system 35, including the monitoring regulation module 23, may reside in the host network 30, as is depicted in the embodiment of FIG. 2.

Figure 2:
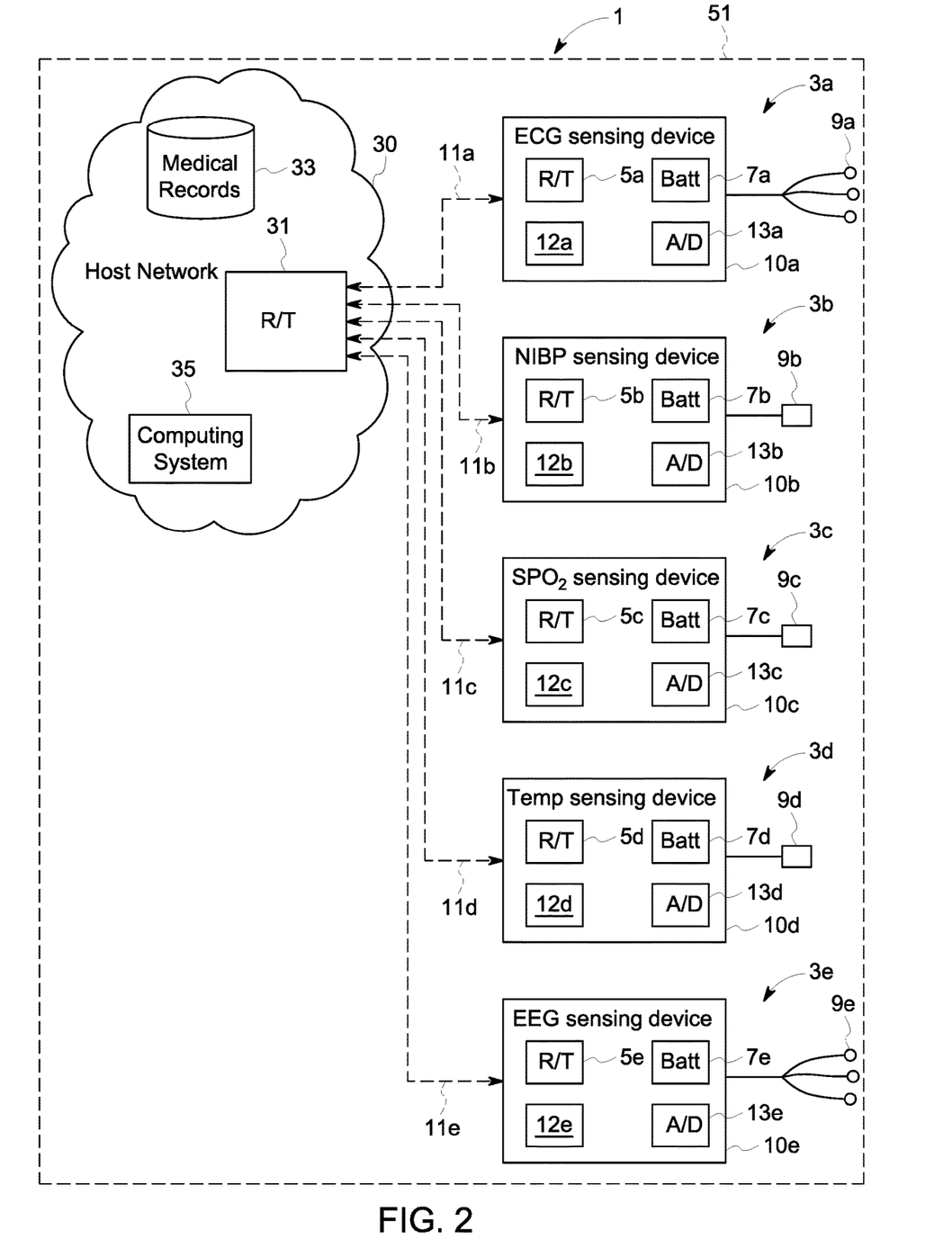
FIG. 2 provides a schematic diagram of another embodiment of a wireless patient monitoring system.

In the embodiment of FIG. 2, the hub device 15 is omitted and the wireless sensing devices 3a-3e communicate directly with the host network 30. Thus, the receiver/transmitter 5a-5e of each wireless sensing device 3a-3e may communicate with a receiver/transmitter 31 associated with the host network 30 by the respective communication link 11a-11e. The communication link 11a-11e in this embodiment may operate according to any wireless communication protocol listed above. It may be desirable to operate the communication according to a wireless communication protocol that is appropriate for longer-range transmission. For example, the wireless sensing devices 3a-3e may communicate with the host network 30 on the WMTS spectrum or on the Wi-Fi spectrum. In such an embodiment, receiver/transmitters 31 may be provided throughout a patient care facility, such as a hospital, as needed based on the system configuration and the location of patients being monitored by wireless sensor devices. The host network 30 may house the computing system 35 containing the monitoring regulation module 23, and thus the calculation of the patient condition index and measurement interval assignment may be conducted by the computing system 35 housed in the host network 30. Further, the host network 30 may provide one or more central monitoring stations, such as user interfaces at central locations for attending clinicians to monitor patient conditions and/or receive alarm notifications.

Figure 3:
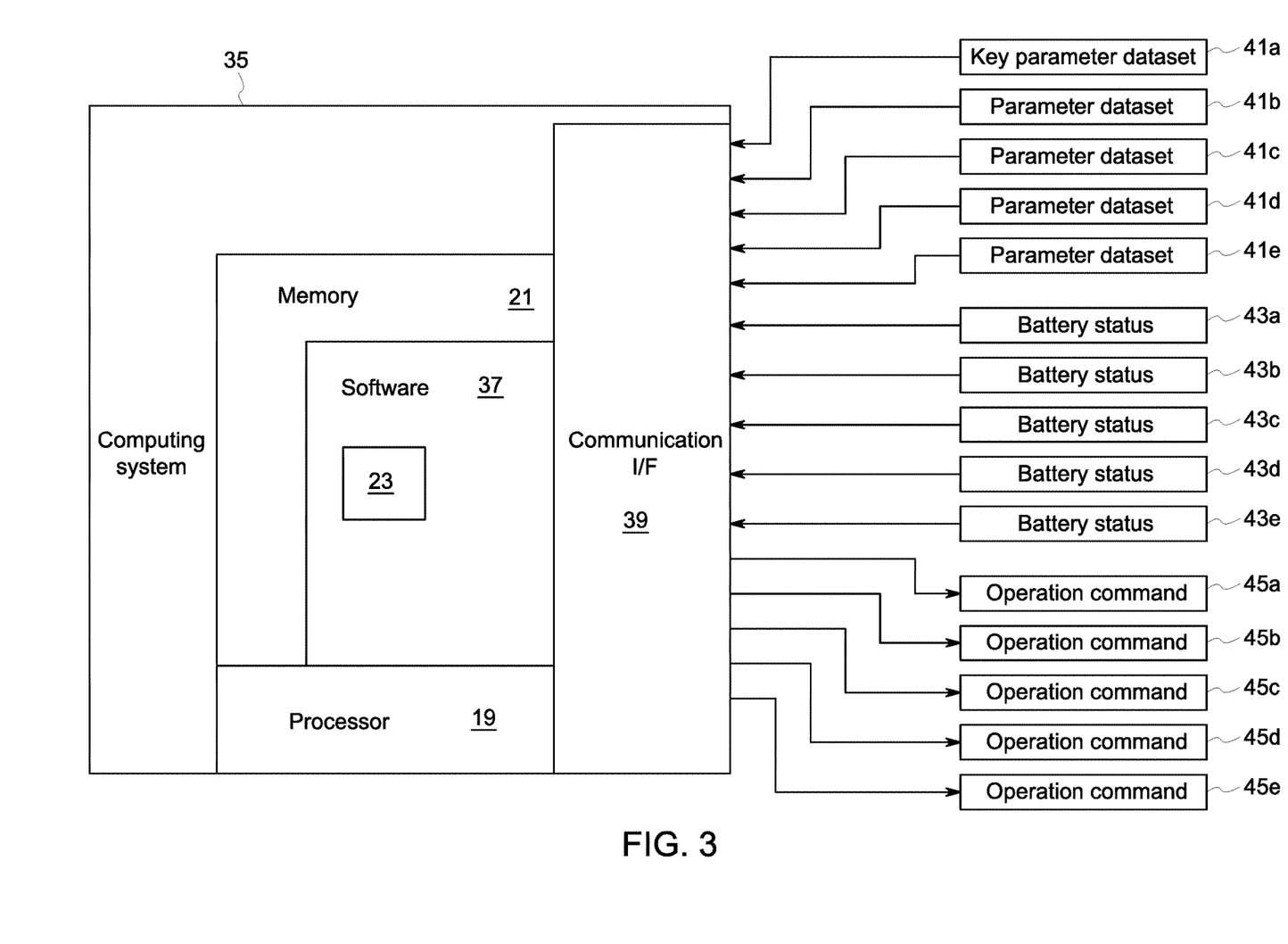
FIG. 3 provides a schematic diagram of one embodiment of a computing system portion of a wireless patient monitoring system of the present disclosure.

FIG. 3 provides a system diagram of an exemplary embodiment of the computing system 35 having a monitoring regulation module 23 executable to control the wireless sensing devices 3a-3e. The computing system 35 includes a processor 19, memory 21, software 37, and communication interface 39. The processor 19 loads and executes software 37 from memory 21, including the monitoring regulation module 23, which is an application within the software 37. Each monitoring regulation module 23 includes computer-readable instructions that, when executed by the computing system 35 (including the processor 19), direct the operation as described in detail herein, including to calculate the patient condition index and assign the measurement intervals for the wireless sensing devices 3a-3e.

Although the computing system 35 as depicted in FIG. 3 includes one software element 37 encapsulating one monitoring regulation module 23, it should be understood that one or more software elements having one or more modules may provide the same operation. Similarly, while the description provided herein refers to a single computing system 35 having a single processor 19, it is to be recognized that implementations of such systems can be performed using one or more processors, which may be communicatively connected, and such implementations are considered to be within the scope of the description. Likewise, the computing system 35 may be implemented as several computing systems networked together, including in a cloud computing environment. Such an embodiment may be utilized, for example, where the computing system 35 is part of the host network 30.

The memory 21, which includes the medical record database 33, can comprise any storage media, or group of storage media, readable by processor 19 and/or capable of storing software 37. The memory 21 can include volatile and non-volatile, removable and non-removable storage media implemented in any method or technology for storage of information, such as computer-readable instructions, data structures, program modules, or other data. Memory 21 can be implemented as a single storage device but may also be implemented across multiple storage devices or sub-systems. For example, the software 37 may be stored on a separate storage device than the medical record database 33. Further, in some embodiments the memory 21 may also store the medical record database 33, which could also be distributed, and/or implemented across one or more storage media or group of storage medias accessible within the host network 30. Similarly, medical record database 33 may encompass multiple different sub-databases at different storage locations and/or containing different information which may be stored in different formats.

Examples of memory devices, or storage media, include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processor 19, or may be distributed in one or more servers, which may be at multiple locations and networked, such as in cloud computing applications and systems. In some implementations, the store media can be a non-transitory storage media. In some implementations, at least a portion of the storage media may be transitory. Memory 21 may further include additional elements, such a controller capable, of communicating with the processor 19.

The communication interface 39 is configured to provide communication between the processor 19 and the various other aspects of the system 1, including the wireless sensing devices 3a-3e to receive the parameter datasets 41a-41e and the battery status 43a-43e of each respective wireless sensing device 3a-3e and to transmit the operation command 45a-45e to each respective wireless sensing device 3a-3e. For example, the communication interface 39 may include the receiver/transmitters 17 and 25, and/or the receiver/transmitter 31 described above with respect to the various depicted embodiments.

Figure 4:
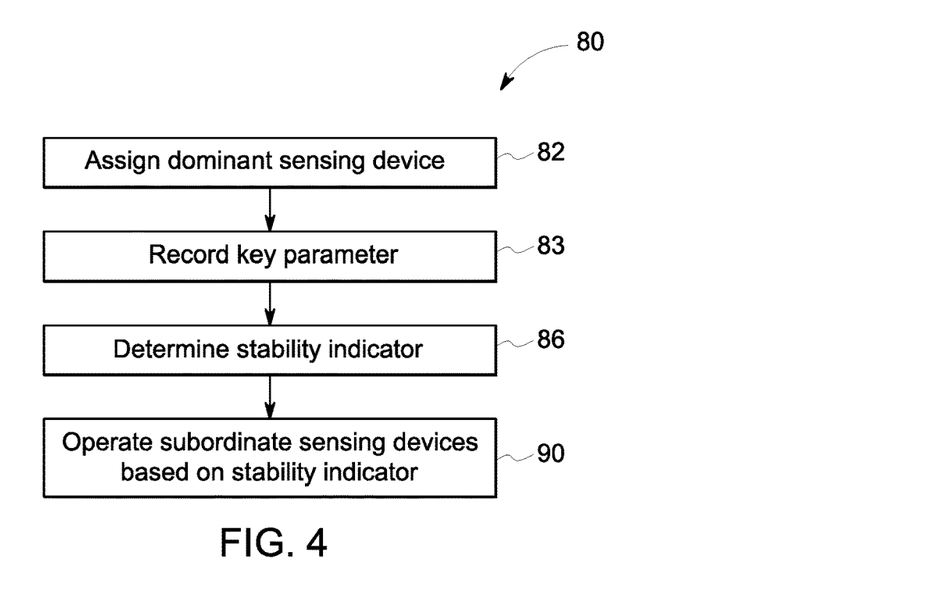
FIG. 4 depicts one embodiment of a method of monitoring a patient.
Figure 5:
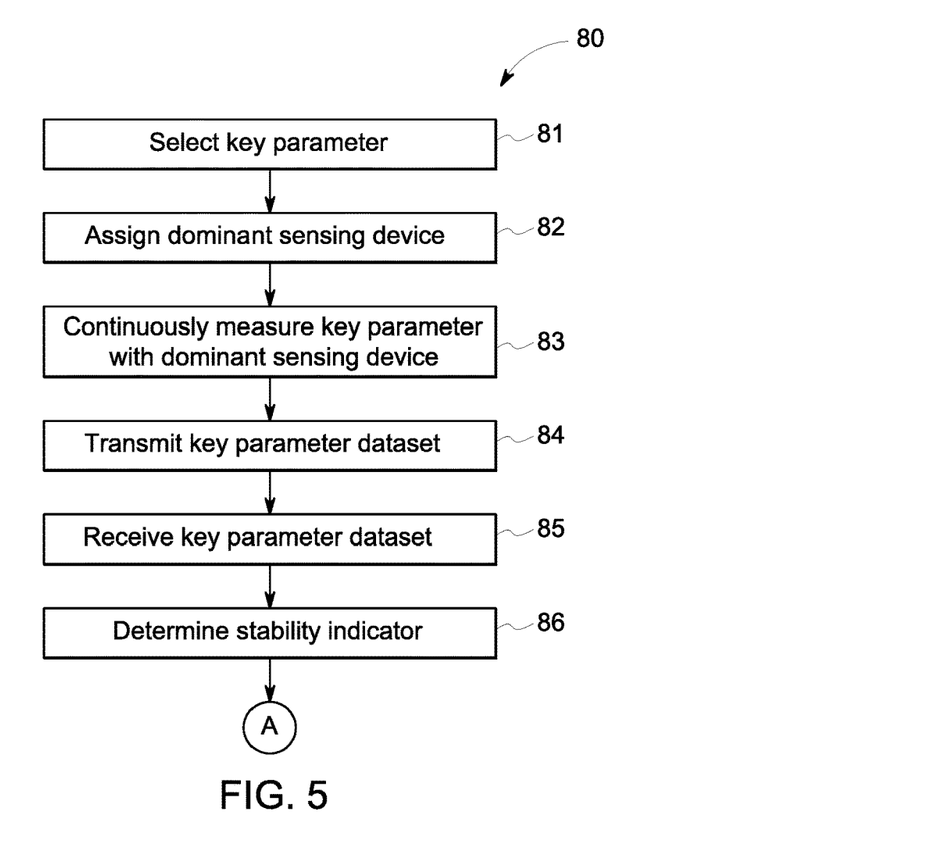
FIGS. 5-8 depict various embodiments of a method of monitoring a patient.

FIG. 4 depicts one embodiment of a method 80 of monitoring a patient. At step 82, a dominant wireless sensing device is assigned. At step 83, a key parameter is recorded from the dominant wireless sensing device, and a stability indicator for the key parameter is determined at step 86. The subordinate sensing devices are then operated at step 90 based on the stability indicator. The operation of the subordinate wireless sensing devices based on the stability indicator may take any number of forms, examples of which are provided in FIGS. 6-8.

FIGS. 5-8 depict other embodiments of the method 80 of monitoring a patient. A key parameter is selected at step 81 and the wireless monitoring device associated with the key parameter is assigned the dominant position at step 82. As explained herein, the dominant wireless sensing device may be assigned, for example, based on a diagnosis for the patient or based on a medical history of the patient. For example, a clinician may input one or more key parameters which will provide the most relevant data for the patient, and the dominant wireless sensing device may then be assigned based on the indicated key parameter. In another embodiment, the key parameter and/or dominant wireless sensing device may be assigned automatically by the system, such as by information provided or accessed in the patient's medical record stored in the medical records database 33. In the depicted embodiment, the key parameter dataset is continuously measured at step 83 and is transmitted at step 84. As described above, other embodiments may operate such that the key parameter is measured with the dominant sensing device at a regular periodic interval. The transmission may also be continuous, or the parameter dataset may be transmitted at predefined intervals. The key parameter dataset is received at step 85 and the stability indicator calculated at step 86. The stability indicator is then used to control the subordinate sensing devices, such as by the method steps exemplified in FIGS. 6-8. At step 81, a key parameter is selected.

Figure 6:
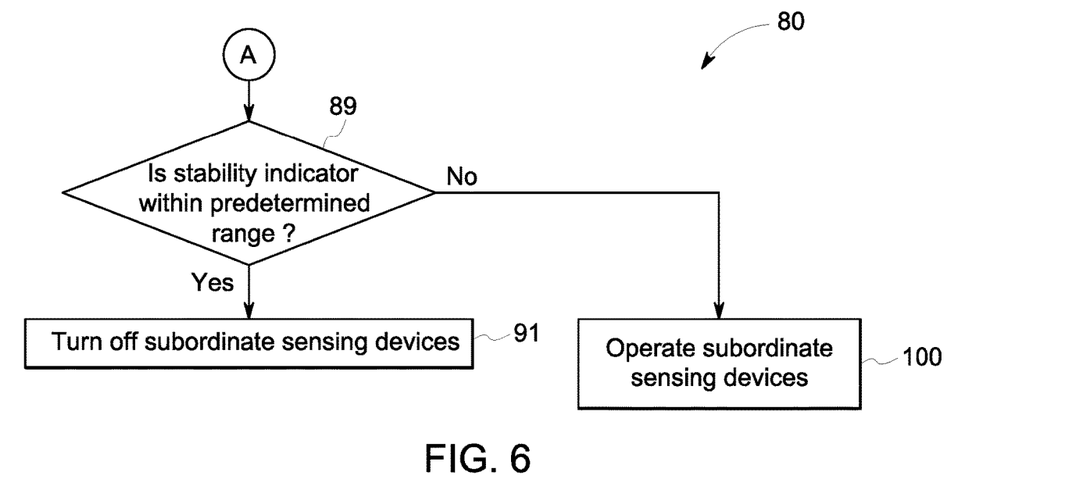

In the embodiment of FIG. 6, the monitoring regulation module 23 determines at step 89 whether the stability indicator calculated at step 86 is within a predetermined range. As described above, the predetermined range for the stability indicator is a range that indicates that the key parameter is stable, which is a proxy for the patient condition as a whole. If the stability indicator is within the predetermined stable range, then one or more of the subordinate sensing devices may be turned off at step 91 such that those subordinate wireless sensing devices no longer measure any physiological parameter from the patient or transmit a parameter dataset. Thus, those subordinate sensing devices that are turned off are utilizing little to no power, other than that used to provide minimal operation to continue receiving relevant operation commands from the computing system 35, such as to wake up the subordinate sensing device if the stability indicator falls out of the predetermined range. If at step 89 the stability indicator is not within the predetermined range, then the subordinate sensing devices may be operated at step 100, such as to continuously monitor the subordinate physiological parameters for a predetermined amount of time, or to measure the subordinate physiological parameters for a predetermined amount of time or to take a predetermined amount of measurements.

Figure 7:
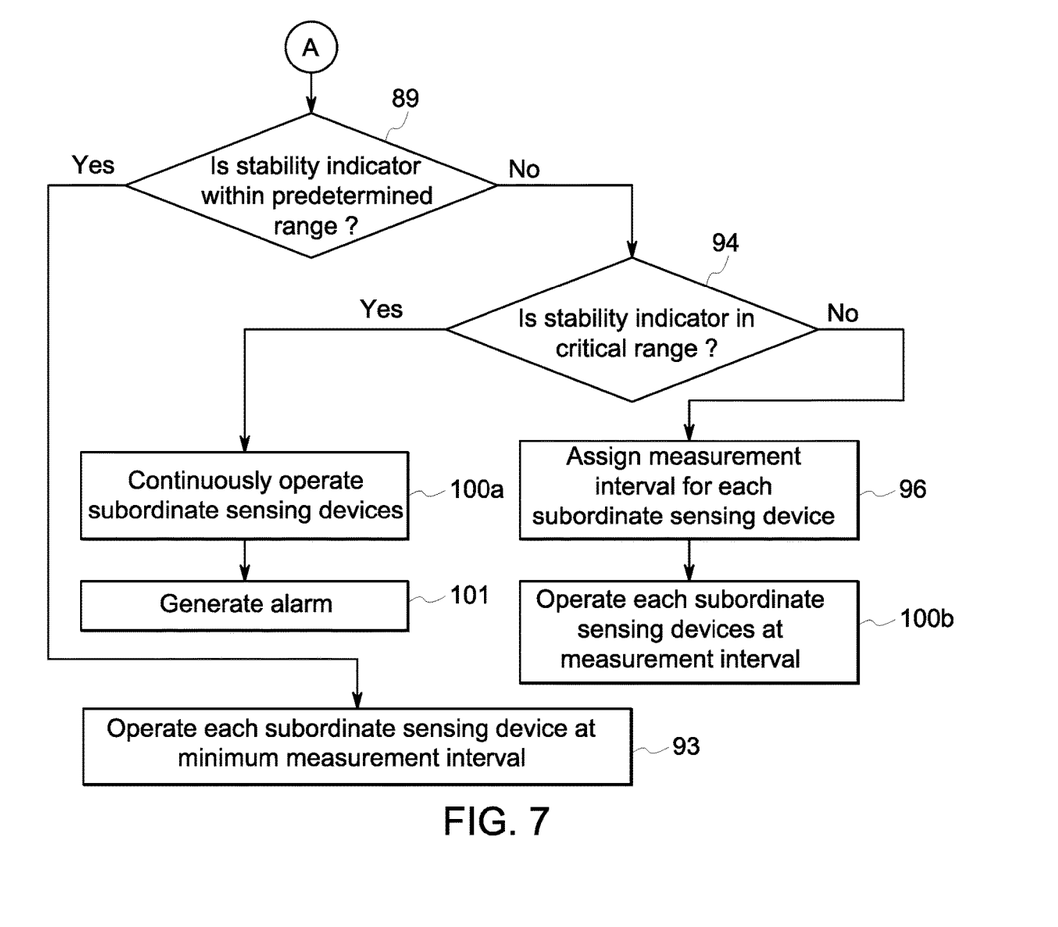

FIG. 7 depicts another embodiment where the subordinate sensing devices are operated at a measurement interval set according to the stability indicator. If the stability indicator is within the predetermined range at step 89, then step 93 may be executed to operate one or more of subordinate sensing devices at the minimum measurement interval for the respective sensing device. As explained above, each subordinate sensing device may have different minimum measurement interval, which may be set based on the type of physiological parameter measured, the patient condition, etc. If at step 89 the stability indicator is not within the predetermined range, the monitoring regulation module 23 may further determine whether the stability indicator is within a predetermined critical range at step 94. If the stability indicator is within a critical range, then the maximum measurement interval, such as continuous monitoring, will be assigned for each of the subordinate sensing devices at step 100a and an alarm will be generated at step 101. If at step 94 the stability indicator is not within the critical range, and is thus somewhere between stable and critical, then an appropriate measurement will be assigned for each subordinate sensing device at step 96 based on the value of the stability indicator. For example, a measurement interval somewhere between the minimum and maximum interval for each subordinate sensing device may be assigned. Each subordinate sensing device is then operated at step 100b according to the assigned measurement interval.

Figure 8:
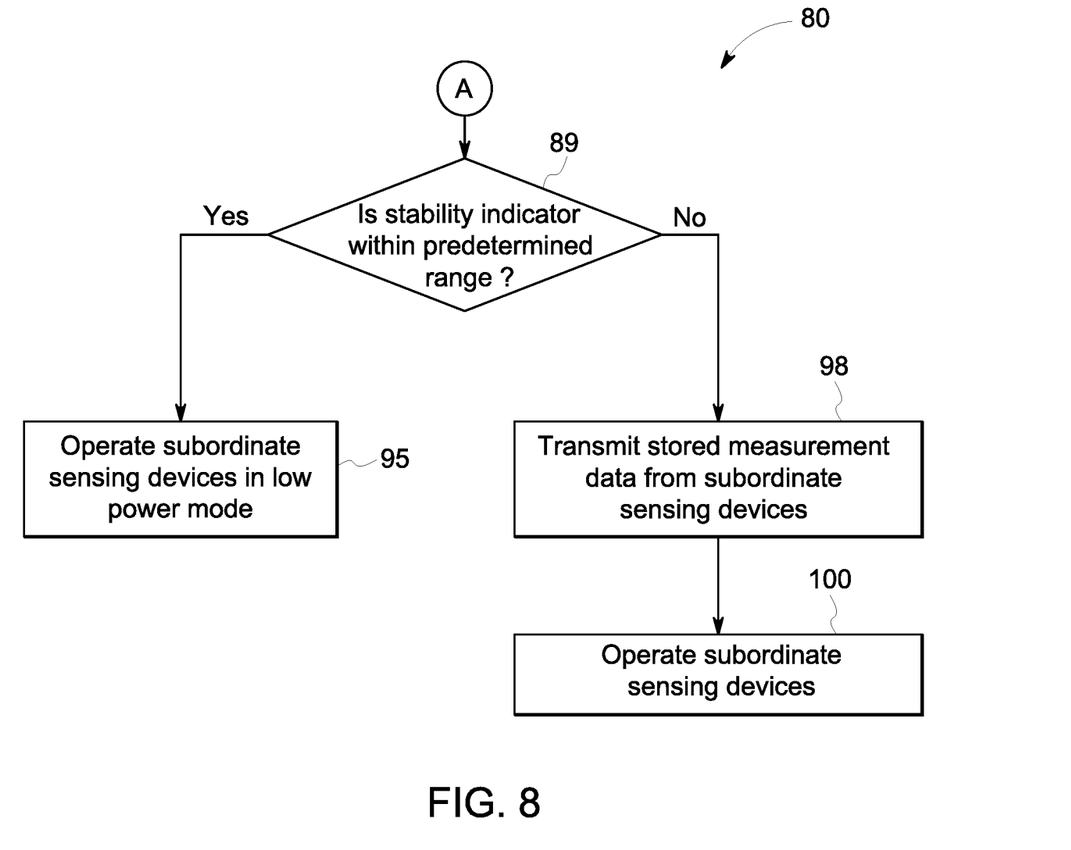

FIG. 8 depicts another embodiment of a method 80 for monitoring a patient where the subordinate sensing devices are operated in a low power mode indicated by step 95, if it is determined at step 89 that the stability indicator is within the predetermined stable range. The subordinate sensing devices may be operated in low power mode to continuously measure the relevant physiological parameters, or may measure the relevant physiological parameters from the patient at a predefined interval. For example, the subordinate wireless sensing devices may keep measuring the relevant physiological parameter from the patient and may store a predetermined amount of the most recent measurement data, but may not transmit the parameter dataset unless instructed to do so by the monitoring regulation module 23. As shown in FIG. 8, the predetermined amount of most recent measurement data stored by the wireless monitoring device may be transmitted if the stability indicator is determined to be outside of the predetermined stability range, as is indicated at step 98. Thus, if an incident occurs with the patient where the key parameter suddenly deteriorates, then monitoring data is available from one or more of the subordinate devices that may also capture the time period of the incident. The subordinate sensing devices may then be operated at step 100 to continually monitor the other parameters from the patient.

Alternatively or additionally, the devices may modify their operation in any number of other ways in order to consume less power when the patient is determined to be stable and less monitoring is needed. For example, each wireless sensing device may transmit a lesser amount of parameter data, such as a most relevant subset of the parameter data, or may transmit at a lesser frequency. In another example, the wireless sensor devices may modify their sensing operation to one that demands less energy, such as by operating fewer sensors or operating the sensors in a way that uses less energy. For instance, a wireless ECG sensing device or a wireless EEG sensing device may reduce the number of leads it measures from. In the example of an ECG sensing device, the device may reduce from a 12-lead operation to a 5-lead operation or a 3-lead operation.

In various embodiments, the monitoring regulation module 23 may employ multiple different methods for controlling the subordinate wireless sensing devices 3a-3e in the monitoring network 51. For example, two or more of the exemplary methods depicted in FIGS. 6-8 may be utilized simultaneously, as each may be employed to control different wireless sensing devices in the monitoring network 51.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A patient monitoring system comprising:
   at least two wireless sensing devices, each wireless sensing device configured to measure a different physiological parameter from a patient and wirelessly transmit a parameter dataset;
   a receiver that receives each parameter dataset from each of the at least two wireless sensing devices;
   a processor;
   a monitoring regulation module executable on the processor to:
      assign one of the at least two wireless sensing devices as a dominant wireless sensing device and at least one of the remaining wireless sensing devices as a subordinate wireless sensing device, wherein the physiological parameter measured by the dominant wireless sensing device is a key parameter and the parameter dataset transmitted by the dominant wireless sensing device is a key parameter dataset;
      determine a stability indicator for the key parameter based on the key parameter dataset from the dominant wireless sensing device; and
      control a measurement operation of the subordinate wireless sensing device to selectively operate based on the stability indicator for the key parameter, including operating the subordinate wireless sensing device to measure the respective physiological parameter in a low power mode when the stability indicator is within a predetermined range.

2. The patient monitoring system of claim 1, wherein the dominant wireless sensing device is operated to continuously measure the key parameter, and a measurement interval for the subordinate wireless sensing device is assigned based on the stability indicator.

3. The patient monitoring system of claim 1, wherein the dominant wireless sensing device is assigned based on one of a diagnosis or a treatment history for the patient.

4. The patient monitoring system of claim 1, wherein the key parameter and dominant wireless sensing device are rotated amongst at least two of the two or more wireless sensing devices.

5. The patient monitoring system of claim 1, wherein controlling the measurement operation of the subordinate wireless sensing device includes changing the measurement operation of the subordinate wireless sensing device to measure the respective physiological parameter upon determining that the stability indicator for the key parameter is outside of a predetermined range.

6. The patient monitoring system of claim 1, wherein the subordinate wireless sensing device in the low power mode measures the respective physiological parameter utilizing a reduced number of sensors.

7. The patient monitoring system of claim 1, wherein the subordinate wireless sensing device in the low power mode measures the respective physiological parameter at a less-frequent measurement interval.

8. The patient monitoring system of claim 1, wherein controlling the measurement operation of the subordinate wireless sensing device includes operating in a low power mode when the stability indicator for the key parameter is within a predetermined range, such that the respective subordinate wireless sensing device does not transmit any parameter dataset.

9. A method of monitoring a patient, the method comprising:
   providing two or more wireless sensing devices, each wireless sensing device configured to measure a different physiological parameter from a patient and communicatively connected to a computing system having a processor;
   assigning at the processor one of the at least two wireless sensing devices as a dominant wireless sensing device and at least one of the remaining wireless sensing devices as a subordinate wireless sensing device;
   operating the dominant wireless sensing device to measure a key parameter from a patient and wirelessly transmit a key parameter dataset;
   determining a stability indicator for the key parameter based on the key parameter dataset; and
   selectively operating the at least one subordinate wireless sensing device based on the stability indicator for the key parameter, including operating at least one of the subordinate wireless sensing devices in a low power mode when the stability indicator for the key parameter is within a predetermined range, wherein the subordinate wireless sensing device in the low power mode measures a physiological parameter from the patient utilizing a reduced number of sensors.

10. The method of claim 9, further comprising operating the dominant wireless sensing device to continuously measure the key parameter; and
   assigning a measurement interval for the subordinate wireless sensing device based on the stability indicator.

11. The method of claim 9, wherein the dominant wireless sensing device is assigned based on one of a diagnosis or a medical history for the patient.

12. The method of claim 9, further comprising assigning a new dominant wireless sensing device by selecting one of the subordinate wireless sensing devices to be the dominant wireless sensing device.

13. The method of claim 12, wherein the new dominant wireless sensing device is assigned based on previously transmitted parameter datasets or based on battery power constraints.

14. The method of claim 9, wherein controlling the measurement operation of the subordinate wireless sensing device includes changing the measurement operation of the subordinate wireless sensing device to measure the respective physiological parameter upon determining that the stability indicator for the key parameter is outside of a predetermined range.

15. The method of claim 9, wherein the subordinate wireless sensing device in the low power mode measures a physiological parameter from the patient at a predefined interval and stores a predetermined amount of most recent measurement data, and does not transmit any parameter dataset.

16. A method of monitoring a patient, the method comprising:

providing two or more wireless sensing devices, each wireless sensing device configured to measure a different physiological parameter from a patient and communicatively connected to a computing system having a processor;

assigning at the processor one of the at least two wireless sensing devices as a dominant wireless sensing device and at least one of the remaining wireless sensing devices as a subordinate wireless sensing device;

operating the dominant wireless sensing device to measure a key parameter from a patient and wirelessly transmit a key parameter dataset;

determining a stability indicator for the key parameter based on the key parameter dataset; and selectively operating the at least one subordinate wireless sensing device based on the stability indicator for the key parameter, wherein selectively operating the subordinate wireless sensing devices includes operating at least one of the subordinate wireless sensing devices when the stability indicator for the key parameter is outside of a predetermined range, wherein the key parameter and dominant wireless sensing device are rotated amongst at least two of the two or more wireless sensing devices.

* * * * *